United States Patent [19]
Kim et al.

[11] Patent Number: 6,075,167
[45] Date of Patent: Jun. 13, 2000

[54] METHOD FOR PREPARING CYCLOALIPHATIC DIAMINES FROM AROMATIC DIAMINES

[75] Inventors: Hoon Sik Kim; Kun Yu Park; Young Soo Kwon; Moon Jo Chung; Byung Gwon Lee, all of Seoul, Rep. of Korea

[73] Assignee: Korea Institute of Science and Technology, Seoul, Rep. of Korea

[21] Appl. No.: 09/160,821

[22] Filed: Sep. 25, 1998

[30] Foreign Application Priority Data

Oct. 7, 1997 [KR] Rep. of Korea ............... 97-51416

[51] Int. Cl.7 .................................................. C07C 209/00
[52] U.S. Cl. ............................................ 564/450; 564/451
[58] Field of Search ........................................ 564/450, 451

[56] References Cited

U.S. PATENT DOCUMENTS 4,394,299  7/1983  Puskas et al. .

*Primary Examiner*—Samuel Barts
*Attorney, Agent, or Firm*—Darby & Darby

[57] ABSTRACT

This invention relates to a method for preparing cycloaliphatic diamines by hydrogenating aromatic diamines in the presence of a supported ruthenium catalyst and a metal nitrite as a catalyst promoter to increase the rate of the hydrogenation reaction and decrease the amount of higher boiler by-products.

16 Claims, No Drawings

METHOD FOR PREPARING CYCLOALIPHATIC DIAMINES FROM AROMATIC DIAMINES

BACKGROUND OF THE INVENTION

1. Field of the Invention

The present invention relates to a preparation method of cycloaliphatic diamine by the hydrogenation of aromatic diamine in the presence of a ruthenium catalyst and a metal nitrite ($MNO_2$) as a catalyst promoter.

2. Description of the Related Art

A polyurethane is a polymer having a carbamate group (—NHCOO—), and is prepared by reacting diisocyanate and polyol such as ethylene glycol. The properties of the polyurethane depend on its raw materials or its preparation method, and especially, the structure of a diamine which is a starting material of the diisocyanate. Urethane polymers derived from aromatic diisocyanates undergo slow oxidation in the presence of air and light, causing a discoloration which is unacceptable in some applications. However, urethane prepared from cycloaliphatic diamine is stable against light and air, as well as structurally flexible, which has better properties compared with urethane prepared from aromatic diamines.

There are substantial literature in the art with respect to the hydrogenation of aromatic amines, especially, methylenedianiline to produce bis(4-aminocyclohexyl)methane, or 1,2-, 1,3-, 1,4-phenylenediamine to produce corresponding cyclohexane diamine. U.S. Pat. No. 2,511,028 and U.S. Pat. No. 2,606,924 disclose a method of preparing bis(4-aminocyclohexyl)methane from methylene dianiline under a pressure of 200–1,000 psig and at a temperature of 80–270° C. in the presence of a noble metal such as ruthenium, rhodium, iridium or mixture thereof or with platinum or palladium, either as a hydroxide, oxide, or the metal itself on an insert support.

U.S. Pat. No. 3,636,108, U.S. Pat. No. 3,697,449 disclose a hydrogenation of an aromatic diamine using a ruthenium impregnated upon a support, wherein the activity and efficiency of the catalyst is increased by treating the catalyst and support with an alkali metal hydroxide or alkoxide. According to these disclosures, such alkali moderation of the catalyst could be effected prior to hydrogenation or in situ during the hydrogenation. They also describe that formation of tars, decomposition products and/or condensation products formed during the hydrogenation can be reduced and that catalyst can be used repeatedly without catalyst regeneration if the catalyst used is a supported ruthenium catalyst which has been alkali-moderated.

U.S. Pat. No. 3,591,635 and U.S. Pat. No. 3,856,862 disclose a method for hydrogenating an aromatic diamine by pretreating rhodium with $NH_4OH$ or in the presence of ammonia. It has been known that, in the early experiment of the hydrogenation of an aniline, ammonia suppressed the formation of by-products, but deactivated the catalyst. It has been reported that similar phenomenon also occurs in the presence of an alkali alkoxide or alkali hydroxide such as LiOH or NaOH.

Further, U.S. Pat. No. 4,946,998 and U.S. Pat. No. 5,214,212 disclose a method for the hydrogenation of an aromatic diamine using a supported ruthenium catalyst modified by NaOH or $FeSO_4 \cdot 7H_2O$ under a high pressure and high temperature.

U.S. Pat. No. 4,448,995 discloses that the hydrogenation reaction should be carried out in an anhydrous state or at least maintained so that water concentration is less than 0.5% by weight to reduce the amount of N-alkylated and higher boiler by-products. In addition, the patent states that lithium salts reduce by-products. However, U.S. Pat. No. 4,946,998 reported that the presence of LiOH increases the production of high molecular weight products.

However, these conventional methods described above are not adequate for industrial processes due to low yields and the requirement of a corrosive base.

Therefore, the present invention is directed to provide a method of preparing cyclodiamine compound by hydrogenating aromatic diamine in the presence of a ruthenium catalyst and metal nitrite. By this invention, the hydrogenation reaction time is significantly shortened and the formation of by-products are greatly suppressed.

DETAILED DESCRIPTION OF THE INVENTION

The present invention relates to a method of preparing a cycloaliphatic diamine by hydrogenating an aromatic diamine compound in the presence of a ruthenium catalyst and a metal nitrite ($MNO_2$) as a catalyst promoter, and under a pressure of about 300 to 4,000 psig and at a temperature of about 50 to 250° C.

Aromatic diamines of the present invention are represented by the general formula (I) as follows:

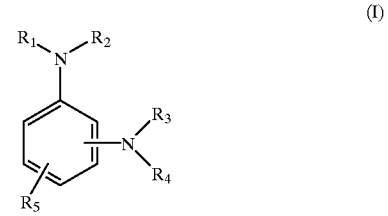

wherein $R_1$, $R_2$, $R_3$, $R_4$ and $R_5$ are H or alkyl group having 1 to 6 carbon atoms, respectively. Examples of amines are 1,2-, 1,3- or 1,4-phenylenediamine, 2,4- or 2,6-toluenediamine, 1-methyl-3,5-diethyl-2,4 or 2,6-diaminobenzene, diisopropyl toluene diamine, tert-butyl-2,4 or 2,6-toluene diamine, xylene diamine, mesitylene diamine and alkyl derivatives thereof, etc.

Alternatively, a compound having a general formula (II) as follows can be used:

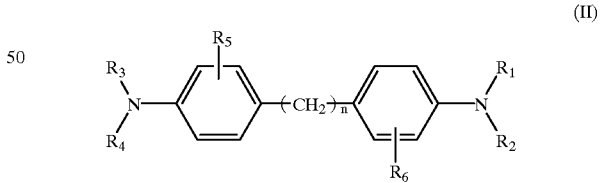

wherein $R_1$, $R_2$, $R_3$, $R_4$, $R_5$, and $R_6$ are H or alkyl group having 1 to 6 carbon atoms, respectively, and $n=0$ or 1. Examples of bridged amines are methylenedianiline, bis(4-amino-2-methylphenyl)methane, O-tolidine, and a secondary or tertiary amine derivatives thereof, etc.

A ruthenium catalyst of the present invention is supported upon an inert carrier. The representative carriers include activated charcoal (C), calcium carbonate ($CaCO_3$), ceria ($CeO_2$), alumina ($Al_2O_3$), zirconia ($ZrO_2$), titania ($TiO_2$) and silica ($SiO_2$). The activated charcoal is the most preferred carrier. The amount of the ruthenium catalyst used is in the range of about 0.05 to 20% by weight based on the starting diamine, and the ruthenium loading on the carrier is about 0.5 to 20% by weight. However, in the consideration of reactivity and economical aspect, the most preferred range of the catalyst amount and the ruthenium loading are 0.1 to 5% and 1 to 10% by weight, respectively.

A metal nitrite which is used as a catalyst promoter in the present invention is selected from the group comprising of barium nitrite [$Ba(NO_2)$], sodium nitrite ($NaNO_2$), potassium nitrite ($KNO_2$) and silver nitrite ($AgNO_2$). The most preferred is $NaNO_2$. The effective amount of the metal nitrite used is in the range from about 1 to 50 times of ruthenium, and preferably about 5 to 20 times.

The present invention may be carried out at any suitable pressure, preferably from about 300 to 4,000 psig. However, considering the equipment and operating cost, it is preferable to operate a reaction at a pressure of 500 to 2,000 psig.

The reaction temperature used for the hydrogenation process range from about 50 to 250° C., preferably from about 100 to 200° C.

The reaction of the present invention may be carried out in the presence of a solvent. Useful solvents include ethers such as diethylether and isopropylether; alcohols such as methanol, ethanol, isopropyl alcohol and butanol, etc.; and cycloethers such as tetrahydrofuran (THF) and dioxane. The most preffered solvent are isopropyl alcohol or n-butanol. The amount of solvent is about 50 to 10,000% by weight based on the amount of diamine, preferably from about 500 to 3,000% by weight.

The hydrogenation of the present invention may be carried out either in a batch or in a continuous process followed by observing the amount of hydrogen taken up by the reaction mixture. The reaction is considered to be terminated when the theoretical amount of hydrogen has been consumed. In general, the hydrogenation time ranges from about 20 to 120 minutes. The longer reaction times at the higher temperatures generally cause an increase in the unwanted by-products.

The invention will be described further in the following examples. These examples are intended for illustrative purposes, and are not intended to limit the scope of the present invention.

EXAMPLE 1

5% Ru/C 1 g (0.5 mmol atom of Ru) and $NaNO_2$ 0.34 g (5 mmol), isopropyl alcohol 25 mL and 1,4-phenylene diamine 5.4 g (50 mmol) were added to a high pressure reactor. The reactor was then sealed and pressurized to 800 psig and heated to 140° C. After reacting for 20 minutes at 140° C., it was cooled to room temperature and then the product was isolated. Analysis of the product, i.e. 1,4-cyclohexane diamine, using a GC and HPLC revealed that the conversion of 1,4-phenylene diamine was 98.3% and the selectivity was 97.5%.

EXAMPLES 2–7

Using various catalyst promoters and changing the amount thereof, experiments were carried out in the same manner as described in Example 1. The results are shown in Table 1.

TABLE 1

| example | promoter | amount of promoter (mmol) | conversion (%) | selectivity (%) |
|---|---|---|---|---|
| 2 | — | — | 75.3 | 84.3 |
| 3 | $Ba(NO_2)_2$ | 5 | 85.7 | 93.1 |
| 4 | $NaNO_2$ | 3 | 81.5 | 91.4 |
| 5 | $NaNO_2$ | 10 | 97.2 | 98.6 |
| 6 | $KNO_2$ | 5 | 89.3 | 95.1 |
| 7 | $AgNO_2$ | 5 | 80.8 | 93 |

EXAMPLES 8–13

Using various reactants, experiments were carried out in the same manner as desribed in Example 1. The results are shown in Table 2.

TABLE 2

| example | reactant | product | time (min) | conversion (%) | selectivity (%) |
|---|---|---|---|---|---|
| 8 | 1,3-phenylene diamine | 1,3-cyclohexane diamine | 20 | 96.5 | 96.5 |
| 9 | 2,4-toluene diamine | 1,3-diamino-4-methyl cyclohexane | 40 | 95.3 | 98.7 |
| 10 | 4,5-diamino-O-xylene | 1,2-diamino-4,5-dimethyl cyclohexane | 40 | 92.1 | 98.4 |
| 11 | bis(4-aminophenyl) methane | bis(4-aminocyclohexyl) methane | 20 | 99.8 | 95.3 |
| 12 | bis(4-amino-2-methyl phenyl) methane | bis(4-amino-2-methyl cyclohexyl) methane | 30 | 97.2 | 92.1 |
| 13 | N,N'-dimethyl-1,4-phenylene diamine | N,N'-dimethyl-1,4-diamino cyclohexane | 30 | 92.5 | 96.5 |

EXAMPLES 14–20

Using various support and changing the amount thereof, experiments were carried out in the same manner as described in Example 1. The results are shown in Table 3.

TABLE 3

| example | support | Ru impregnated amount (wt %) | conversion (%) |
|---|---|---|---|
| 14 | activated charcoal | 1 | 42.5 |
| 15 | activated charcoal | 10 | 100 |
| 16 | alumina | 3 | 61.7 |
| 17 | alumina | 5 | 89.4 |
| 18 | titania | 5 | 51.2 |
| 19 | silica | 5 | 73.7 |
| 20 | ceria | 5 | 53.8 |

EXAMPLES 21–26

Using various solvents, experiments were carried out in the same manner as described in Example 1. The results are shown in Table 4.

TABLE 4

| example | solvent | conversion (%) | selectivity (%) |
|---|---|---|---|
| 21 | methanol | 93.1 | 68.5 |
| 22 | ethanol | 95.3 | 73.4 |
| 23 | diethylether | 47.2 | 85.7 |
| 24 | THF | 58.1 | 83.4 |
| 25 | dioxane | 37.9 | 81.6 |
| 26 | n-butanol | 90.3 | 96.5 |

EXAMPLES 27–31

Under various pressures and temperatures, experiments were carried out in the same manner as described in Example 1. The results are shown in Table 5.

TABLE 5

| example | temperature (° C.) | pressure (psig) | conversion (%) | selectivity (%) |
|---|---|---|---|---|
| 27 | 100 | 1000 | 23.7 | 72.1 |
| 28 | 120 | 1000 | 67.1 | 83.7 |
| 29 | 140 | 500 | 90.4 | 96.7 |
| 30 | 140 | 2000 | 99.5 | 92.8 |
| 31 | 200 | 800 | 100 | 81.6 |

Although the preferred embodiments of the present invention have been disclosed for illustrative purposes, those skilled in the art will appreciate that various modifications, additions and substitutions are possible, without departing from the scope and spirit of the invention as recited in the accompanying claims.

What is claimed is:

1. A method of preparing cycloaliphatic diamines by hydrogenating an aromatic diamine in an organic solvent in the presence of a supported ruthenium catalyst, wherein a metal nitrite is used as a catalyst promoter.

2. The method of claim 1, wherein the metal nitrite is selected from the group consisting of $Ba(NO_2)_2$, $NaNO_2$, $KNO_2$ and $AgNo_2$.

3. The method according to claim 2, wherein the metal nitrite is $NaNO_2$.

4. The method according to claim 1, wherein an amount of the metal nitrite used is 1 to 50 times based on a mole of ruthenium.

5. The method according to claim 4, wherein the amount of the metal nitrite used is 5 to 20 times based on the mole of ruthenium.

6. The method according to claim 1, wherein a temperature of the hydrogenation is 50 to 250° C.

7. The method of preparing the cycloaliphatic diamines according to claim 6, wherein the temperature of the hydrogenation is 100 to 200° C.

8. The method according to claim 1, wherein a pressure of the hydrogenation is 300 to 4,000 psig.

9. The method according to claim 8, wherein the pressure of the hydrogenation is 500 to 2,000 psig.

10. The method according to claim 1, wherein an amount of the ruthenium catalyst is 0.1 to 5 wt % based on the aromatic diamine.

11. The method of claim 1, wherein the ruthenium catalyst is impregnated into a carrier, and wherein the carrier is selected from the group consisting of activated charcoal, calcium carbonate, ceria, alumina, zirconia, titania and silica.

12. The method according to claim 11, wherein the ruthenium catalyst is impregnated with 1 to 10 wt % of the carrier.

13. The method of claim 1, wherein the organic solvent is an alcohol, an ether or a cycloether.

14. The method of claim 13, wherein said alcohol is methanol, ethanol, isopropyl alcohol or butanol.

15. The method of claim 13, wherein said ether is diethylether or isopropylether.

16. The method of claim 13, wherein said cycloether is tetrahydrofuran or dioxane.

* * * * *